(12) United States Patent
Jin et al.

(10) Patent No.: US 12,607,507 B2
(45) Date of Patent: Apr. 21, 2026

(54) AUTONOMOUS PHENOTYPE IMAGING SYSTEM

(71) Applicant: Purdue Research Foundation, West Lafayette, IN (US)

(72) Inventors: Jian Jin, West Lafayette, IN (US); Ziling Chen, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 110 days.

(21) Appl. No.: 18/387,991

(22) Filed: Nov. 8, 2023

(65) Prior Publication Data

US 2024/0151581 A1 May 9, 2024

Related U.S. Application Data

(60) Provisional application No. 63/423,773, filed on Nov. 8, 2022.

(51) Int. Cl.
    *G01J 3/02*        (2006.01)
    *G01J 3/28*        (2006.01)
    (Continued)

(52) U.S. Cl.
    CPC ........... *G01J 3/0278* (2013.01); *G01J 3/0237* (2013.01); *G01J 3/0291* (2013.01); *G01J 3/2823* (2013.01);
    (Continued)

(58) Field of Classification Search
    CPC ........ G01J 3/0202; G01J 3/021; G01J 3/0237; G01J 3/0262; G01J 3/0264; G01J 3/0278;
    (Continued)

(56) References Cited

U.S. PATENT DOCUMENTS

| | | | |
|---|---|---|---|
| 2018/0010964 A1* | 1/2018 | Chen ...................... | G01J 3/0208 |
| 2019/0107440 A1* | 4/2019 | Pluvinage ............. | G01J 3/0297 |

(Continued)

OTHER PUBLICATIONS

Zhang et al., (2019). Optimized angles of the swing hyperspectral imaging system for single corn plant. Computers and Electronics in Agriculture, 156, 349-359.

(Continued)

*Primary Examiner* — Jason Holloway
*Assistant Examiner* — Blake A Wood
(74) *Attorney, Agent, or Firm* — Piroozi-IP, LLC

(57) ABSTRACT

An autonomous system for providing consistent images of leaves of plants is disclosed which includes a mobility system configured to move from an originating position to a position above a plant in a field, a robotic system coupled to the mobility system, the robotic system includes a manipulator providing a plurality of degrees of freedom, and an imaging system having an imaging chamber and one or more cameras, the imaging system coupled to the manipulator, the manipulator and the imaging system cooperate to position the imaging system about a leaf of a plant such that the manipulator articulates the imaging chamber substantially parallel and in line with the leaf and further moves the imaging system so that the leaf enters the imaging chamber thereby allowing the imaging system to obtain images of the leaf.

22 Claims, 17 Drawing Sheets
(9 of 17 Drawing Sheet(s) Filed in Color)

(51) Int. Cl.

| | | |
|---|---|---|
| *G01N 21/84* | (2006.01) | |
| *G01N 33/00* | (2006.01) | |
| *G03B 15/03* | (2021.01) | |
| *G06V 20/10* | (2022.01) | |
| *H04N 13/10* | (2018.01) | |
| *H04N 13/204* | (2018.01) | |

(52) U.S. Cl.
CPC ......... *G01N 33/0098* (2013.01); *G03B 15/03* (2013.01); *G06V 20/194* (2022.01); *H04N 13/10* (2018.05); *H04N 13/204* (2018.05); *G01N 2021/8466* (2013.01)

(58) Field of Classification Search
CPC .......... G01J 3/0291; G01J 3/10; G01J 3/2823; G01J 2003/104; G01J 2003/2826; G01N 33/0098; G01N 2021/8466; G06V 20/194; H04N 13/10; H04N 13/204
See application file for complete search history.

(56) References Cited

U.S. PATENT DOCUMENTS

| | | | | |
|---|---|---|---|---|
| 2020/0294620 | A1* | 9/2020 | Bauer | ................... G06V 20/188 |
| 2024/0057527 | A1* | 2/2024 | Karydis | ................... A01G 3/00 |

OTHER PUBLICATIONS

Zhang et al., (2019). Establishment of Plot-Yield Prediction Models in Soybean Breeding Programs Using UAV-Based Hyperspectral Remote Sensing. Remote Sensing, 11(23).

Zheng et al., (2012). Leaf orientation retrieval from terrestrial laser scanning (TLS) data. IEEE Transactions on Geoscience and Remote Sensing, 50(10), 3970-3979.

Geldhof et al., (2021). A digital sensor to measure real-time leaf movements and detect abiotic stress in plants. Plant Physiology, 187(3), 1131-1148.

Zhang et al., (2012). Robust hyperspectral vision-based classification for multi-season weed mapping. ISPRS Journal of Photogrammetry and Remote Sensing, 69, 65-73.

Li et al., (2022). Robotic crop row tracking around weeds using cereal-specific features. Computers and Electronics in Agriculture, 197, 106941.

Blad et al., (1972). Orientation and distribution of leaves within soybean canopies. Agronomy Journal, 64(1), 26-29.

Biskup et al., (2007). A stereo imaging system for measuring structural parameters of plant canopies. Plant, Cell Environment, 30(10).

Wang et al., LeafScope: A Portable High-Resolution Multispectral Imager for In Vivo Imaging Soybean Leaf. Sensors, 20(8), 2194.

Jinendra et al., (2010). Near infrared spectroscopy and aquaphotomics: Novel approach for rapid in vivo diagnosis of virus infected soybean. Biochemical and Biophysical Research Communications, 397(4), 685-690.

Bradley et al., (2021). Soybean Yield Loss Estimates Due to Diseases in the United States and Ontario, Canada, from 2015 to 2019. Plant Health Progress, 22(4), 483-495.

Chen et al., (2021). Automated in-field leaf-level hyperspectral imaging of corn plants using a Cartesian robotic platform. Computers and Electronics in Agriculture, 183, 105996.

Cui et al., (2009). Detection of soybean rust using a multispectral image sensor. Sensing and Instrumentation for Food Quality and Safety, 3(1), 49-56.

Da Silva Junior et al., (2018). Soybean varieties discrimination using non-imaging hyperspectral sensor. Infrared Physics and Technology, 89, 338-350.

Fletcher et al., (2016). Random forest and leaf multispectral reflectance data to differentiate three soybean varieties from two pigweeds. Computers and Electronics in Agriculture, 128, 199-206.

Gowen et al., (2007). Hyperspectral imaging—an emerging process analytical tool for food quality and safety control. Trends in Food Science and Technology, 18(12), 590-598.

Gui et al., (2021). Grading method of soybean mosaic disease based on hyperspectral imaging technology. Information Processing in Agriculture, 8(3), 380-385.

Guilherme et al., (2021). Using leaf-based hyperspectral reflectance for genotype classification within a soybean germplasm collection assessed under different levels of water availability. International Journal of Remote Sensing, 42(21), 8165-8184.

Kao et al., (1992). Dirunal leaf movement, chlorophyll fluorescence and carbon assimilation in soybean grown under different nitrogen and water availabilities. Plant, Cell & Environment, 15(6), 703-710.

Kovar et al., (2019). Evaluation of hyperspectral reflectance parameters to assess the leaf water content in soybean. Water (Switzerland), 11(3), 1-12.

Ma et al., (2021a). Modeling of diurnal changing patterns in airborne crop remote sensing images. Remote Sensing, 13(9), 1-19.

Pandey et al., (2017). High Throughput In vivo Analysis of Plant Leaf Chemical Properties Using Hyperspectral Imaging. Frontiers in Plant Science, 8, 1348.

Rehman et al., (2020). Calibration transfer across multiple hyperspectral imaging-based plant phenotyping systems: I—Spectral space adjustment. Computers and Electronics in Agriculture, 176, 105685.

Wang (2021). Automated Leaf-Level Hyperspectral Imaging of Soybean Plants using an UAV with a 6 DOF Robotic Arm.

Wang et al., (2020). LeafSpec: An accurate and portable hyperspectral corn leaf imager. Computers and Electronics in Agriculture, 169, 105209.

Yuan et al., (2017). Retrieving Soybean Leaf Area Index from Unmanned Aerial Vehicle Hyperspectral Remote Sensing: Analysis of RF, ANN, and SVM Regression Models. Remote Sensing, 9(4).

Zhang et al., (2019). Assessing crop damage from dicamba on non-dicamba-tolerant soybean by hyperspectral imaging through machine learning. Pest Management Science, 75(12), 3260-3272.

\* cited by examiner

200

Leaf Tip
Leaf Base
Leaf Center
Plant Center
Target Leaf Tip
Leaflet

Moving Direction

Moving Direction

Plastic
Dampers

AUTONOMOUS PHENOTYPE IMAGING SYSTEM

CROSS-REFERENCE TO RELATED APPLICATIONS

The present non-provisional patent application is related to and claims the priority benefit of U.S. Provisional Patent Application Ser. No. 63/423,773, filed Nov. 8, 2022, the contents of which are hereby incorporated by reference in its entirety into the present disclosure.

STATEMENT REGARDING GOVERNMENT FUNDING

None.

TECHNICAL FIELD

The present disclosure generally relates to plant phenotypic systems, and in particular to a plant phenotyping imaging system with an automatic leaf-handling mechanism.

BACKGROUND

This section introduces aspects that may help facilitate a better understanding of the disclosure. Accordingly, these statements are to be read in this light and are not to be understood as admissions about what is or is not prior art.

A high throughput plant phenotyping system is required for plant researchers and precision agriculture in order improve high yields and also develop new genotype as well as to monitor plant health. Specifically, precision agriculture is now ubiquitously used to optimize crop yield especially in light of decades-long drought conditions in vast areas of the country by using systems with feedback to provide water where needed, improve monitoring of crop health, and minimizing environmental impact by optimizing fertilizers and insecticides to only area where these potentially harmful chemicals are deemed to be necessary. Furthermore, where new plants are being planted, it is necessary to understand and quantify plant growth and structure at a large scale.

In order to accurately quantify phenotyping over small and large areas, hyperspectral or multispectral imaging systems have been used to image plants in close range. Such systems require large human interaction. For example, a person taking these images needs to manipulate a leaf and the plant to improve image quality. However, by human intervention, significant error is introduced by way of varying levels of leaf and plant manipulation and inconsistency. Suppose a particular type of plant requires a certain angle with respect to lens of the image system to obtain the most amount of information. Human interactions inherently introduces inconsistencies that can result in reduced imaging quality. Additionally, different plants have different leaves with varying levels of toughness. Some plant leaves are easily damaged by rough-handling resulting in damage to the plant as well as further inconsistency in image quality.

Additionally, current Hyperspectral Imaging remote sensing solutions suffer from changing ambient lighting conditions, long imaging distances, and comparatively low resolutions. Recently, handheld hyperspectral imagers were developed to improve the imaging quality. However, the operation of these devices are still limited by its low throughput and intensive labor cost.

Furthermore, automatic leaf-handling mechanisms suffer from inconsistently accepting leaves into an imaging chamber; thus, resulting in loss of quality and necessity for repeating the imaging procedures.

Therefore, there is an unmet need for a novel imaging system that can provide consistent phenotyping images of a large number of plants and their associated leaves to be used for high precision agriculture and phenotyping studies such that leaves of plants are processed consistently.

SUMMARY

An autonomous system for providing consistent images of leaves of plants is disclosed. The system includes a mobility system configured to move from an originating position to a position above a plant in a field. The system further includes a robotic system coupled to the mobility system. The robotic system includes a manipulator providing a plurality of degrees of freedom, and an imaging system having an imaging chamber and one or more cameras. The imaging system coupled to the manipulator, the manipulator and the imaging system cooperate to position the imaging system about a leaf of a plant such that the manipulator articulates the imaging chamber substantially parallel and in line with the leaf and further moves the imaging system so that the leaf enters the imaging chamber thereby allowing the imaging system to obtain images of the leaf.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 4b is a mask used to remove the background information presented in FIG. 4a.

DETAILED DESCRIPTION

Figure 1A:
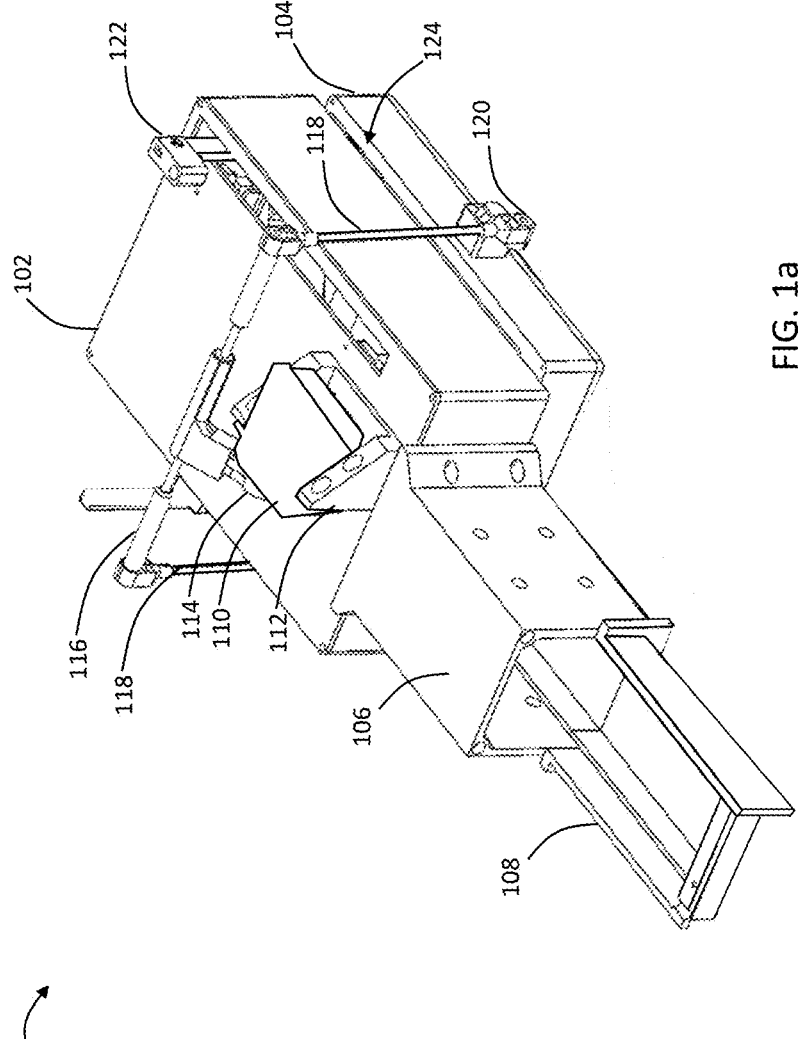
FIG. 1a is an imaging system capable of inserting a leaf into an imaging chamber and providing a consistent environment for imaging followed by obtaining a hyperspectral or multispectral images followed by releasing the leaf without harming the plant.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

A novel imaging system is disclosed herein that can provide consistent phenotyping images of a large number of plants and their associated leaves to be used for high precision agriculture and phenotyping studies such that leaves of plants are processed consistently. Towards this end, a new robotic system is presented operating as a sensor platform for obtaining leaf-level hyperspectral or multispectral images for in vivo plant, e.g., soybean, phenotyping. A machine vision algorithm is presented therefor to be used with a 3D camera to detect the top mature (fully developed) trifoliate and estimate the poses of the leaflets. A control and path planning algorithm is also presented for an articulated robotic manipulator to consistently grasp the target leaflets. An experiment was conducted in a greenhouse with 64 soybean plants of 2 genotypes and 2 nitrogen treatments. The disclosed robotic system with its machine vision detected the target leaflets with a first trial success rate of 84.13% and an overall success rate of 90.66%. The robotic system imaged the target leaflets with a first trial success rate of 87.30% and an overall success rate of 93.65%. The average cycle time for 1 soybean plant was 63.20s. The data collected by the system had a correlation of 0.85 with a manually collected data approach.

The novel imaging system includes a leaf imaging system and a plant imaging system. The leaf imaging system images the leaf in a closed imaging chamber with a hyperspectral camera, multispectral camera, or both after a robot arm manipulates the leaf into the chamber. The plant imaging system images the entire plant with a hyperspectral camera, mithispectral camera, or both while the ambient light is blocked off. A GPS module and a micro-controller are mounted the imaging system. The controller processes the image and uploads the predicted plant health parameters to a remote server together with the geolocation and time stamp data of the images. The remote server monitors plant health over a large area with timelines at farm-level, plot-level, or county level.

Referring to FIG. 1*a*, an imaging system 100 is disclosed. The imaging system 100 as further described below is capable of inserting a leaf into an imaging chamber and providing a consistent environment for imaging followed by obtaining a hyperspectral images, multispectral images, or both followed by releasing the leaf without harming the plant.

A hyperspectral image includes a large number (in hundreds) of color bands. A hyperspectral imaging system uses a grating (similar to a Newton's prism) to spread different colors into different directions, so the different colors end up at different locations on a charge-coupled device (CCD) or a complementary metal oxide semiconductor (CMOS) sensor, thereby measuring different colors with different pixels on the camera sensor. A multispectral image has typically 4-10 color bands resulting from light emitting diodes (LEDs) of different colors in the imaging chamber. By alternating through these LEDs (i.e., turn on one color, and keep all the other colors off) and take one shot for each color and obtaining different images therefrom, the multispectral imaging eventually combines all the frames of different colors into one multispectral image. In the case of a hyperspectral image obtained from a hyperspectral camera, a scanning approach is used to scan the imaging area line-by-line. However, in the case of a multispectral image, the multispectral camera is stationary. It should be appreciated that while not an efficient use of a hyperspectral camera, a hyperspectral camera can be used to obtain both a hyperspectral image and one or more multispectral images. Therefore, for various applications, it may be possible to use only one hyperspectral camera for both imaging modalities.

Figure 1B:
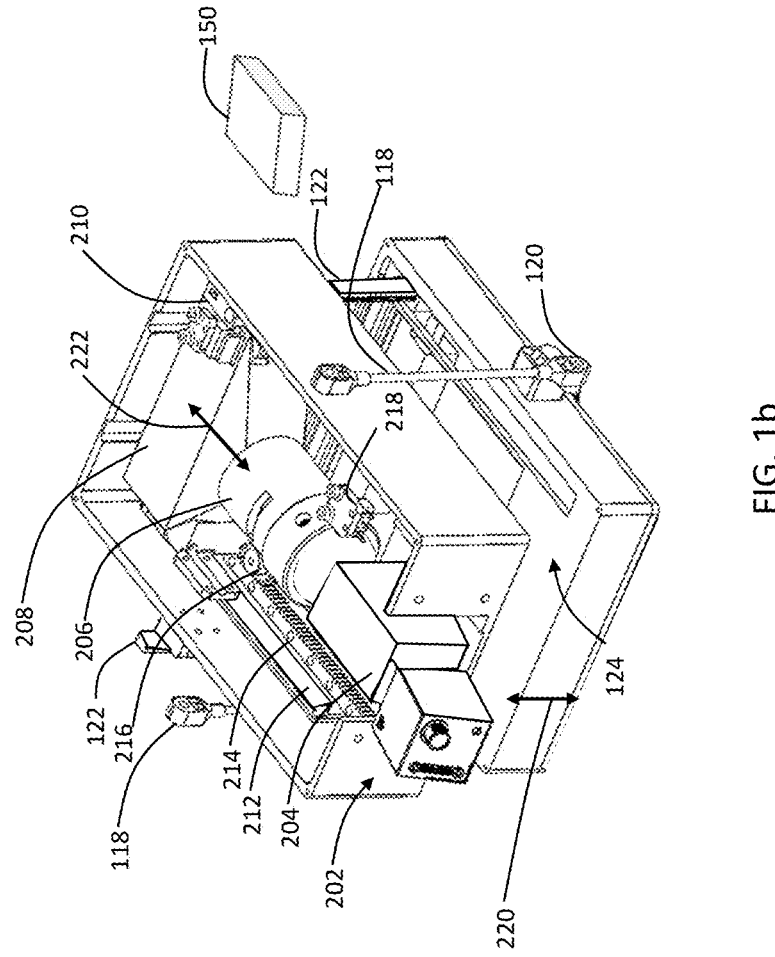
FIG. 1b is a perspective view of the imaging system shown in FIG. 1a with top removed to reveal the components within the upper case.

With reference to FIG. 1*a*, the imaging system 100 according to the present disclosure is described. FIG. 1*a* is a perspective view of the imaging system 100 which includes an upper case 102 and a lower case 104 adapted to articulate with respect to the upper case 102. The imaging system 100 includes a camera housing 106 within which a camera 202 shown in FIG. 1*b* is disposed. The camera 202 shown in FIG. 1*b* is a hyperspectral camera coupled to a linear actuator, further described below. However, in addition to the camera 202 other cameras (not shown) including i) a multispectral camera, ii) an RGB camera, and iii) a depth cam can be implemented in the camera housing 106 for obtaining multispectral images and used in the machine vision approach, discussed below. In the case of having a hyperspectral camera, the camera housing 106 terminates to a camera tray 108 adapted to house various electronics accompanied with the camera 202. A servo motor 110 is attached to motor brackets 112 which are firmly attached to the upper case 102. The servo motor 110 is adapted to rotate a first arm 114. The servo motor 110 can be a stepper motor, an alternating current (AC) motor, a direct current (DC) motor, or a variety of other motors accompanied with motor-drive controls known to a person having ordinary skill in the art. The first arm 114 is coupled to a second arm 116 which is coupled to a pair of third arms 118 that are coupled to the lower case 104 via bearings 120. The combination of the servo motor, the first arm 114, the second arm 116, the pair of third arms 118, and the bearings 120 allow rotational movement of the servo motor 110 to be translated to horizontal and vertical articulation of the lower case 104 with respect to the upper case 102 via a slider-crank mechanism, known to a person having ordinary skill in the art. The speed of the slider-crank mechanism is much faster than a simple linear actuator because the angle of the servo motor 110 can be controlled by a pulse width modulation (PWM) signal or using a stepper motor based on a digital input. While not shown, a limit bumper can provide a limit for vertical travel of the lower case 104 with respect to the upper case 102. A pair of guides 122 provide motion guidance for the lower case 104. In FIG. 1a, an imaging chamber 124 is shown in the collapsed position (i.e., the lower case 104 has articulated with respect to the upper case 102).

Referring to FIG. 1b, a perspective view of the imaging system 100 is shown with top removed to reveal the components within the upper case 102. As discussed above, the upper case includes a camera 202 which includes one or more cameras (e.g., a hyperspectral camera, a multispectral camera, or both; however, only one hyperspectral camera is shown in FIG. 1b), camera base 204 and a lens assembly 206. The lens assembly is optically coupled to a mirror housing 208 adapted to convey light from the imaging chamber 124 to the camera 202. It should be appreciated that a plurality of LEDs (not shown) may be disposed in the lower case 104 configured to provide light with different wavelengths (i.e., colors) to the mirror housing 208 through a leaf 150 that is positioned in the imaging chamber 124 for light travelling through the leaf 150. Additionally, one or more LEDs (not shown) again with different wavelengths (i.e., colors) may be disposed in the upper case 102 adapted to shine light at the leaf 150 for reflection off the leaf 150 and onto the mirror housing.

As described above, the imaging system 100 for hyperspectral imaging is based on scanning line-by-line. Towards this end a linear actuator is employed capable of moving the camera 202 and the mirror housing 208 along a horizontal plane 222. The description below relates to only the linear actuator used with a hyperspectral camera; however, it should be appreciated that if a multispectral is the only camera used, then the linear actuator can be avoided altogether. In cases where both a hyperspectral camera and a multispectral camera are used in the same imaging system 100, then the linear actuator described below is implemented alongside the multispectral camera (not shown) in order to linearly articulate the hyperspectral camera. According to one embodiment, a rack and pinion system known to a person having ordinary skill in the art is employed as the linear actuator to generate said articulation, however, other systems can be used including a lead screw, a belt drive, or a chain drive, all of which are known to a person having ordinary skill in the art. On a horizontal rail 212 a rack 214 is mounted. The rack 214 includes a plurality of gear teeth (e.g., 20 teeth with a pitch distance of 16 mm). A pinion 216 with circular gear teeth is coupled to an actuator (not shown, e.g., a micro metal gear motor with a 1000:1 gear ratio with physical dimension of 29.5 mm×10 mm×12 mm (length× width×height) having a light weight, e.g., 10.5 grams, producing a maximum torque of 11 kg cm which is sufficient to cause linear movement of the aforementioned components). The pinion 216 is adapted to engage with the teeth on the rack 214 and cause the assembly of the camera 202 and the mirror housing 208 to move along the direction 222 for the aforementioned line-scanning. A limit switch 210 is adapted to electronically engage the actuator (not shown) to stop the linear motion thereby avoiding excess linear travel. The camera 202 includes a camera connector 218 which provides electronic signals associated with hyperspectral or multispectral images. The camera connector 218 may provide these electronic signals via a wired connection (e.g., a ribbon cable) or based on a wireless protocol, in each case to a computing device further described below. The vertical articulation of the lower case 104 with respect to the upper case 102 is shown via the double arrow 220.

Figure 1C:
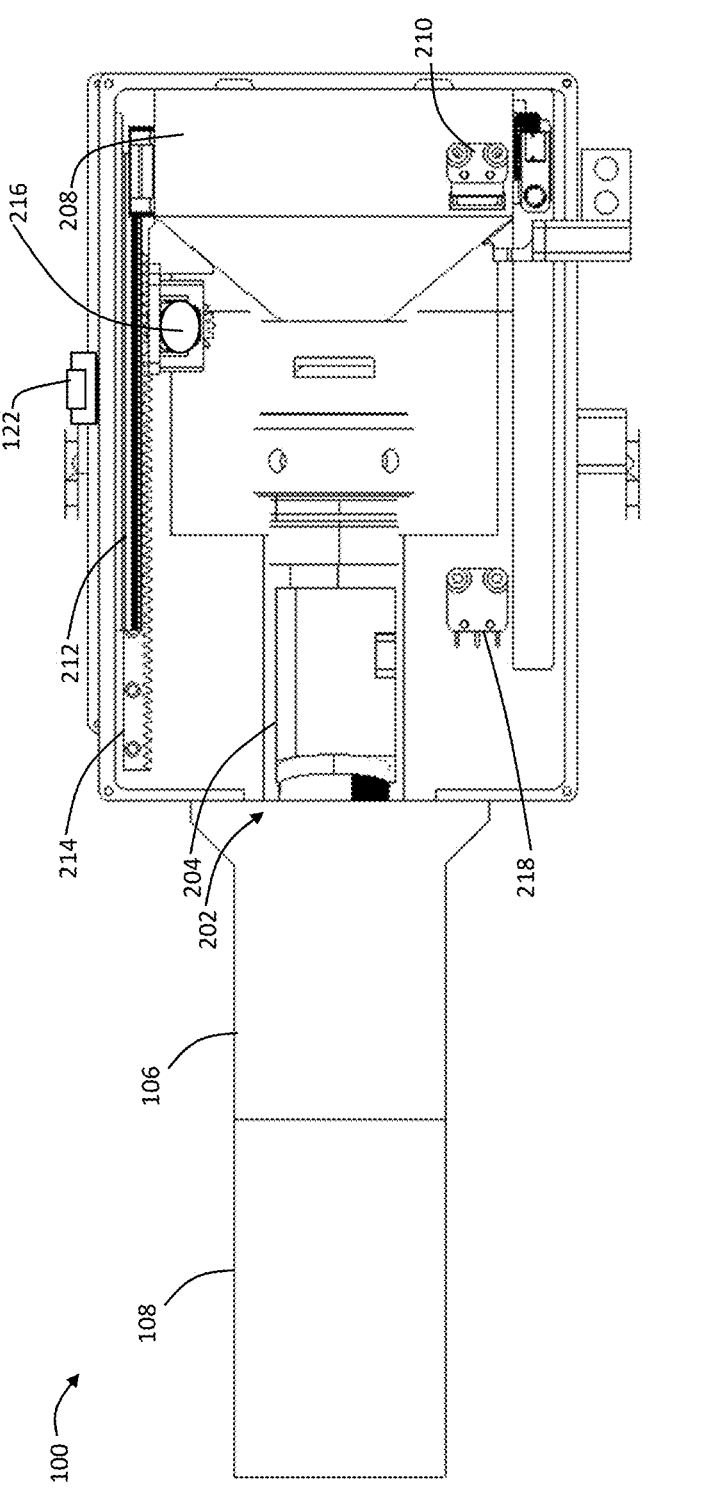
FIG. 1c is a top view of the imaging system if FIG. 1a with the top of the upper case removed to better elucidate the internal components.

Referring to FIG. 1c, a top view of the imaging system 100 is provided, again with top of the upper case 102 removed to better elucidate the internal components. In FIG. 1c, it is better revealed how the camera base 204 is adapted to enter the camera housing 106 during the linear movement of the camera 202 and the mirror housing 208.

Figure 1D:
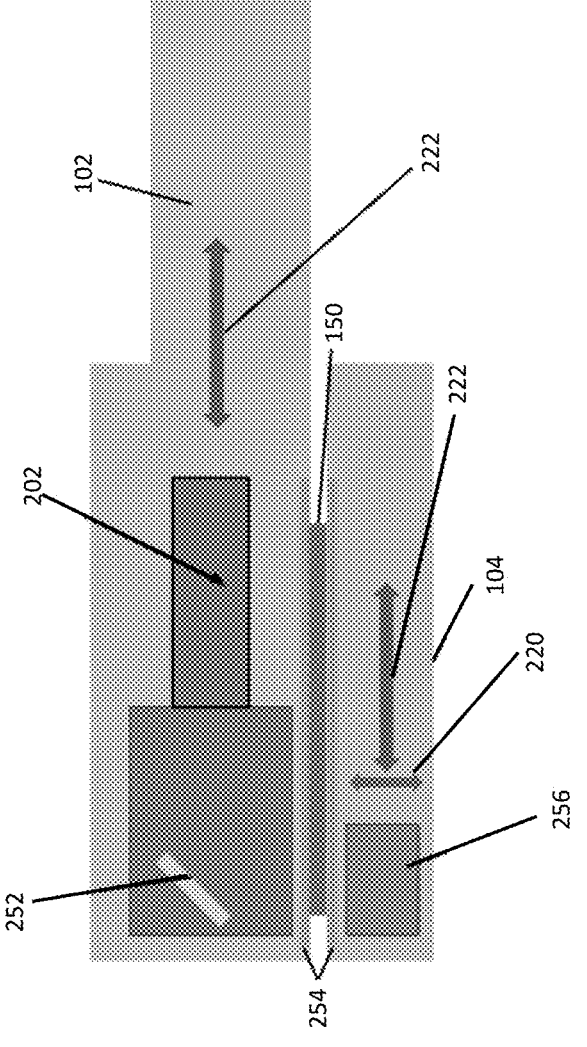
FIG. 1d is a schematic of the imaging system of FIG. 1a revealing the position of a mirror within the mirror housing as well a light box in the lower case adapted to house light sources, e.g., a plurality of light emitting diodes (LEDs), not shown and/or halogen lights, not shown.

Referring to FIG. 1d, a schematic of the imaging system 100 is shown. This figure reveals the position of a mirror 252 within the mirror housing 208 as well a light box 256 in the lower case 104 adapted to house light sources, e.g., the plurality of the above-described LEDs (not shown) and/or halogen lights. Two translucent, e.g., glass, plates 254 are provided (one coupled to the upper case 102 and one coupled to the lower case 104). While not shown, a linear guideway mounting vertically couples the camera 202 to the light box 256. This linear guideway (not shown) allows the light box 256 and the camera 202 to move in concert with one-another, horizontally. Thus, the light box 256 is adapted to horizontally move in concert with the camera 202 in order to enhance illumination of the leaf 150 as the camera 202 moves within the upper case 102. These translucent plates 254 are adapted to provide a consistent imaging environment for the hyperspectral imaging, multispectral imaging, or both while allowing light to travel from the light box 256 through the leaf 150 and to the mirror 252. The material for the translucent plates 254 can be anything that is translucent, e.g., glass, plexiglass, or other such materials known to a person having ordinary skill in the art. It should be appreciated that while vertical distance in FIG. 1c between the translucent plates 254 and the leaf 150 appear to be minimal (i.e., it appears that the glass plates 254 are touching the leaf 150), as described above a second limit switch (not shown) can be implemented to limit this vertical relationship to avoid contact with the leaf 150. In one embodiment, the vertical distance is maintained at a minimum of the range of between about 3 mm to about 10 mm (i.e., between the two translucent plates 254). It should be appreciated that the space within the imaging chamber 124 is dark to prevent optical noise for improved consistency. Therefore, blinds (not shown) are employed all around the imaging chamber 124 in order to darken the space within when the lower case 104 in the articulated position with respect to the upper case 102 as shown in FIG. 1a.

Figure 2:
FIG. 2 is an image of a robotic system for handling a leaf of a plant and imaging that leaf.
Figure 6A:
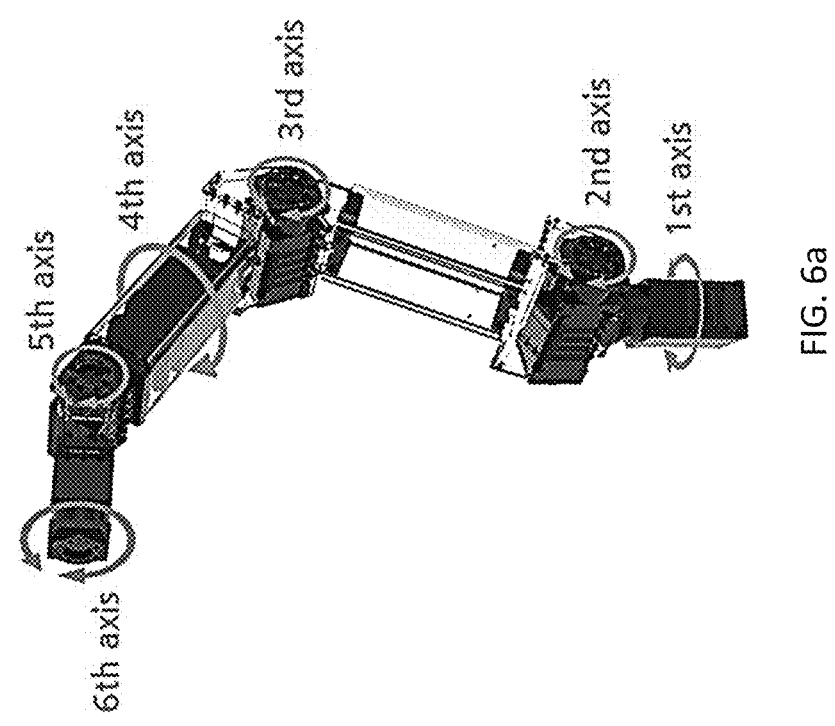
FIG. 6a is a schematic of a robotic arm for operating the imaging system according to the present disclosure.

A robotic system 200 shown in FIG. 2 includes the imaging system 100 (see FIG. 1a) which is coupled with an INTEL REALSENS D435 3D camera (INTEL CORPORATION, U.S.), an OPENMANIPULATOR-P 6-joint articulated robotic manipulator (ROBOTIS CO. LTD, KOREA), see FIG. 6a which is a schematic of the OPENMANIPULATOR-P) for operating the imaging system 100, an NVIDIA JETSON AGX XAVIER computer (NVIDIA CORPORATION, U.S.) with ROBOTIC OPERATING SYSTEM (ROS) MELODIC. It should be noted that while a 6-joint articulated robotic manipulator is shown in FIG. 6a and discussed herein, other numbers of degrees of freedom (i.e., less, e.g., 4; or more) can also be implemented. A machine vision algorithm for detecting target leaflets and a control and path planning algorithm for approaching and grasping the leaflets are disclosed herein which were deployed on AGX. The robotic manipulator was invertedly hung to maximize its coverage and simulate the operating environment of being mounted on a mobile platform for in-field applications. The INTEL REALSENS D435 3D camera was installed at the elbow of the OPENMANIPULATOR-P to have a clear sight without potential collision issues. The robotic system 200 was powered by a 24V power supply connected to a regular outlet.

Referring to FIG. 2, the robotic system 200 is shown in operation as it approaches a leaf and thereby placing the leaf within it imaging chamber 124 (see FIG. 1*b*).

A machine vision module using an INTEL REALSENSE D435 camera (machine vision camera) was used to detect target leaflets and estimate their poses. The machine vision camera was controlled by ROS messages for convenience in data communication. For each image acquisition, the machine vision camera captured a top view of a soybean plant with an RGB image and a depth map. The returned data were processed to detect the pose (x, y, z, roll, pitch, yaw) of the terminal leaflet (mid leaflet) within the top mature trifoliate which is considered the most representative leaf in soybean phenotyping.

Figure 3:
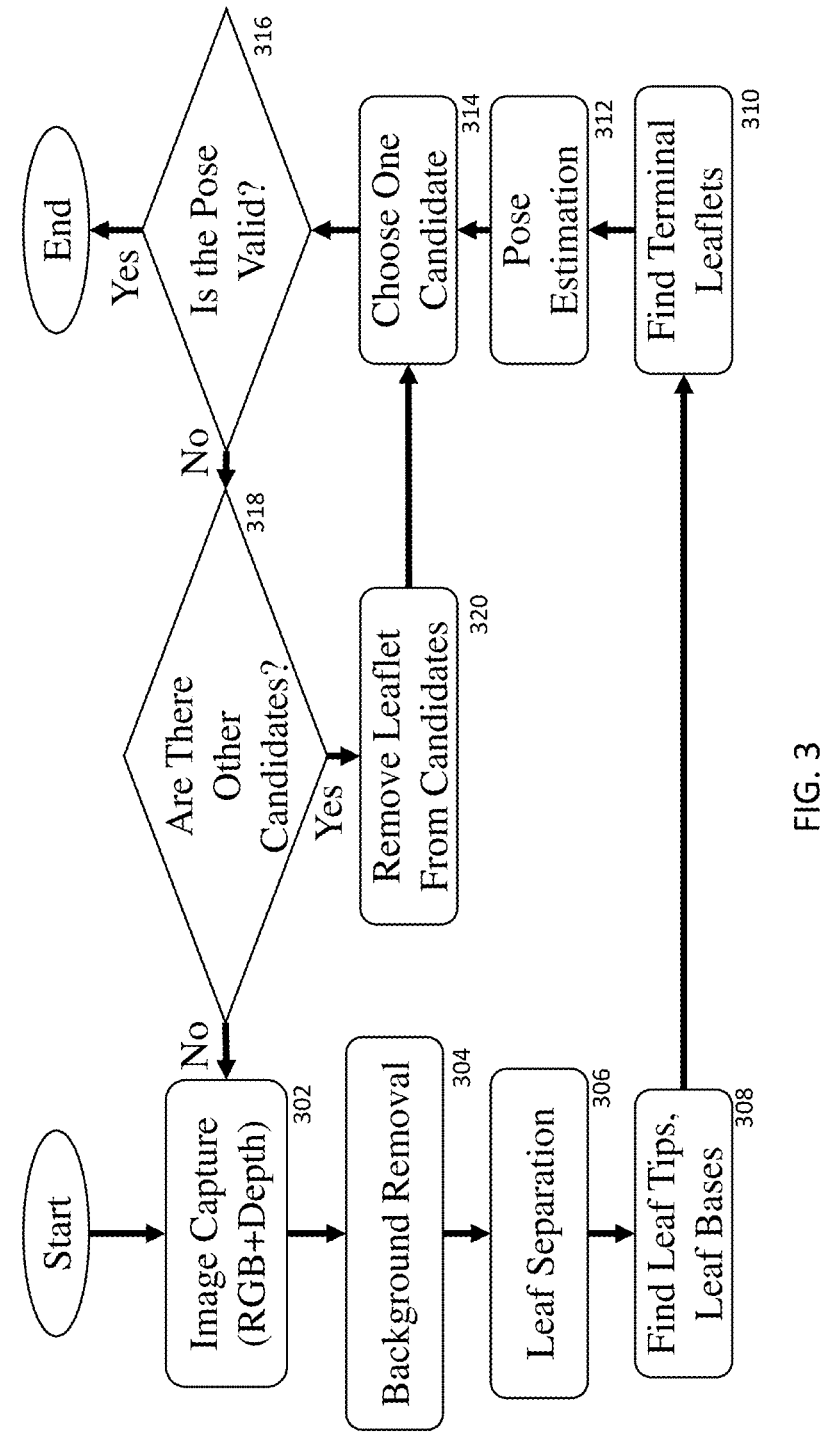
FIG. 3 is a flowchart that forms the basis for the machine vision module, according to the present disclosure.

Referring to FIG. 3, a flowchart 300 is presented that forms the basis for the machine vision module. First an RGB image with depth information is captured as provided in 302. A background removal submodule 304 is then utilized using the depth information provided from the machine vision camera. Since the plant's upper leaves are closer to the machine vision camera in the top view than the soils and the floor, the backgrounds (soils, lower leaves, stems, etc.) in each RGB image (shown in FIG. 4*a* which is a photograph of a plant with the background to be removed) are removed by a mask created from thresholding the corresponding depth map (shown in FIG. 4*b* which is a mask used to remove the background information presented in FIG. 4*a*). The developed machine vision uses 3D information from the machine vision camera to filter out the background, gradients of the 3D information to segment each leaflet, and the ratio between each leaflet's height and area to determine the top matured leaflets. The endpoints are also determined for each leaflet by calculating the furthest two points. To determine which one of the two endpoints is the leaf tip, the positional relationship between the endpoints are compared. However, the results of this background removal contain noise from different sources, because of the mismatched pixels between the RGB image and the depth map. Thus, a greenness indicator was calculated for each pixel using equation (1) for a more refined result.

$$G = g^2/rb \qquad (1)$$

where G is the calculated greenness value; and
r, g, and b are the values of the 3 channels in an RGB image.

Figure 4A:
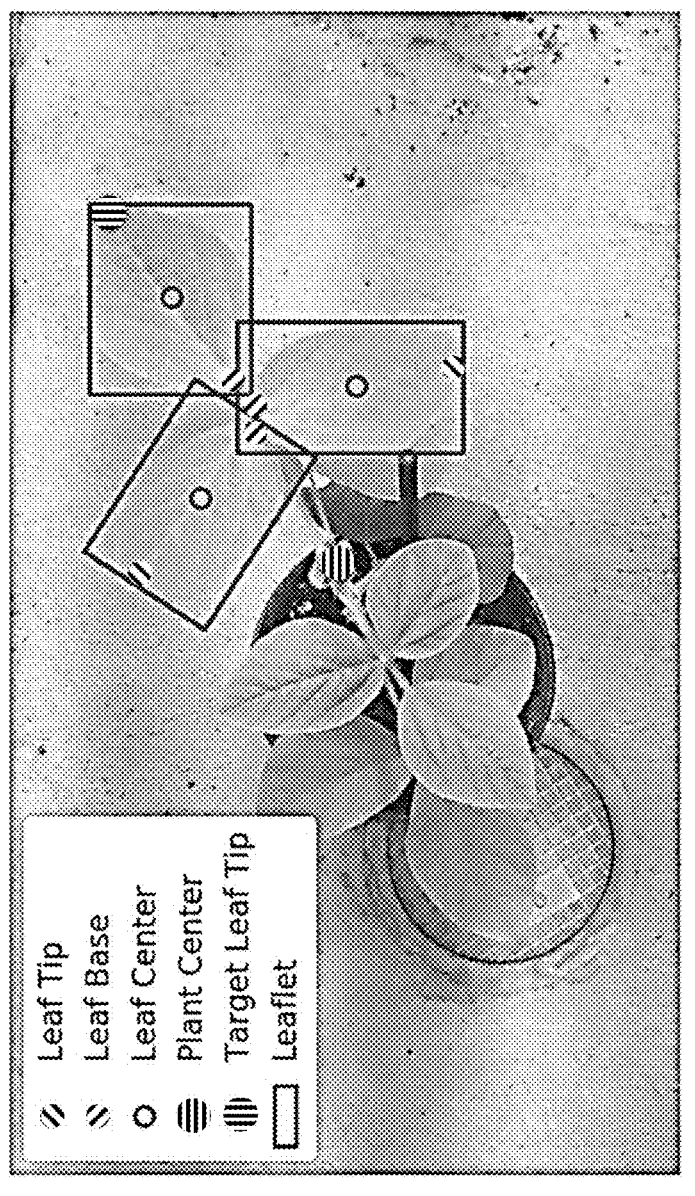
FIG. 4a is a photograph of a plant with its background to be removed.
Figure 4C:
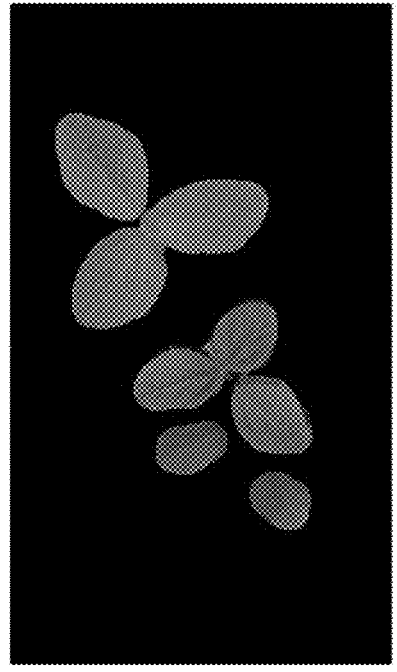
FIG. 4c is an image after background shown in FIG. 4a has been removed using depth map and greenness indicator.
Figure 4B:
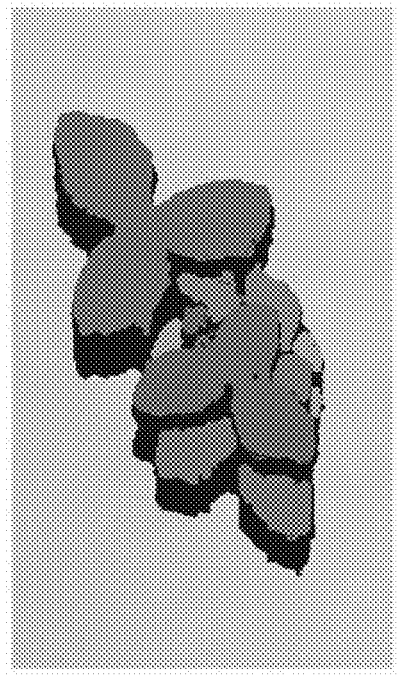
Figure 5:
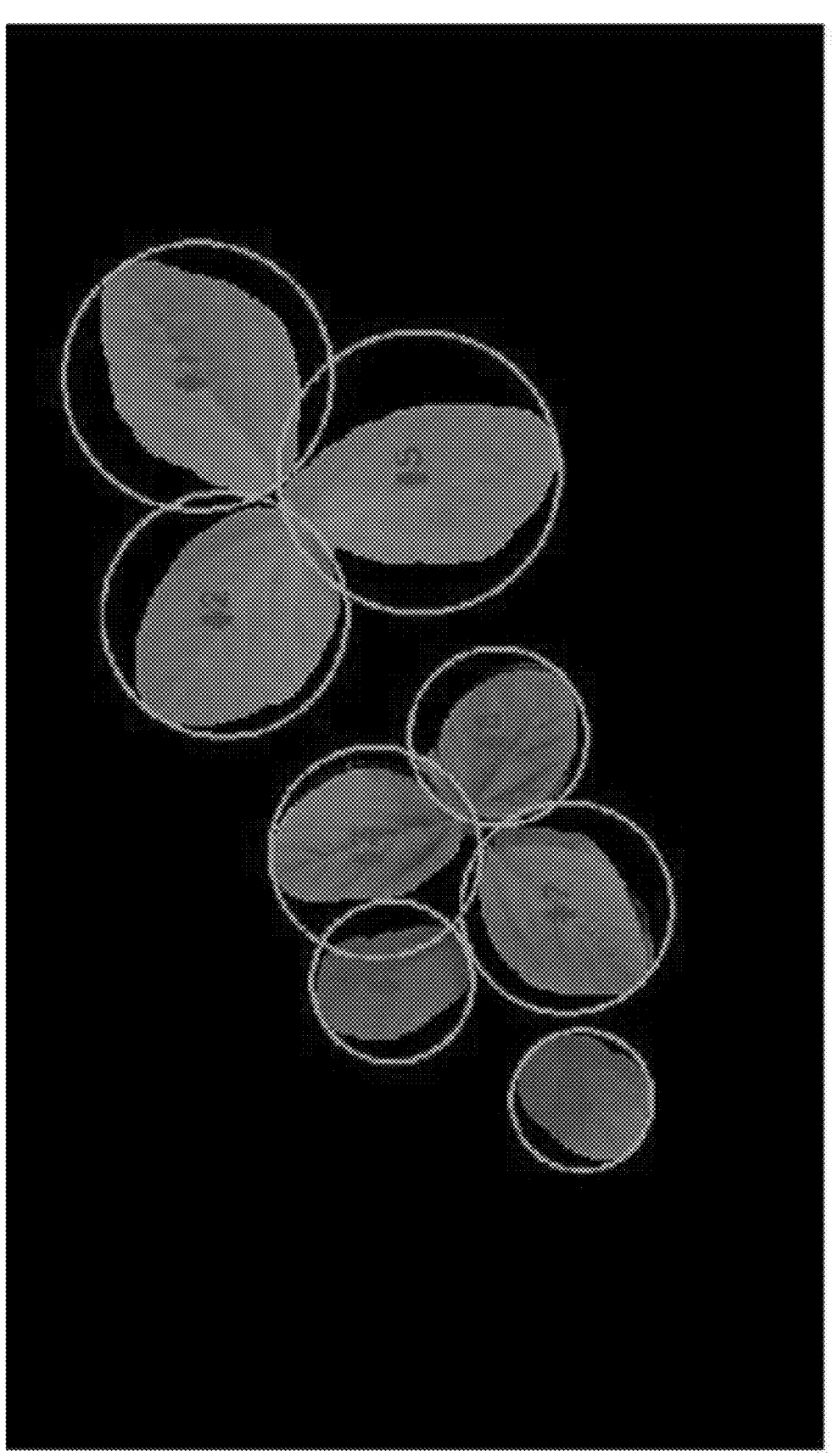
FIG. 5 is am image showing the result from the algorithm of FIG. 3 with leaflets separated (circles) and numbered (numbers).

FIG. 4*c* is an image after background shown in FIG. 4*a* has been removed using depth map and greenness indicator, while FIG. 5 provides the result from the algorithm with leaflets separated (circles) and numbered (numbers).

The image shown in FIG. 4*a* was then processed by thresholding the depth maps and was segmented using the calculated greenness map. The segmented result (see FIG. 4*c*) contained mostly leaflets, but the leaflets were not properly separated because of connected stems or overlaps. Thus, the algorithm 300 uses Euclidean Distance Transform to obtain individual leaflets as shown in FIG. 5, and provided as the leaf separation submodule 306 and find leaf tops and leaf bases submodule 308 in the algorithm 300. Each separated leaflet with its leaf top and leaf bas information is compared using its relative position with others to detect the a target terminal leaflet as provided by submodule 310 in algorithm 300. The orientation of each leaflet is determined by a vector from its base to its tip. While not shown in algorithm, the orientation (i.e., pose) of a finally chosen leaflet can be used to provide micro-adjustment for the mobile imaging system 102 to micro-adjust position of the mobile imaging system 102, according to the present disclosure.

The pose of the target terminal leaflet is next estimated using the pixel coordinates of the tip and base of the leaflet, as provided in the pose estimation submodule 312. With their pixel coordinates known, the depth map, and the machine vision camera's projection matrix, the relative position $(x_r, y_r, z_r)$ between the vertices and the robotic manipulator are calculated using equation (2), which is a standard transformation from the pixel coordinates to the physical coordinates, as it is known to a person having ordinary skill in the art.

$$\begin{bmatrix} du \\ dv \\ d \end{bmatrix} = KT \begin{bmatrix} x_r \\ y_r \\ z_r \\ 1 \end{bmatrix} = \begin{bmatrix} f_x & 0 & c_x \\ 0 & f_y & c_y \\ 0 & 0 & 1 \end{bmatrix} \begin{bmatrix} a_{11} & a_{12} & a_{13} & t_1 \\ a_{21} & a_{22} & a_{23} & t_2 \\ a_{31} & a_{32} & a_{33} & t_3 \end{bmatrix} \begin{bmatrix} x_r \\ y_r \\ z_r \\ 1 \end{bmatrix} \qquad (2)$$

where u and v are the pixel coordinates;
matrix K is the camera's projection matrix;
matrix T is the transformation matrix from the manipulator coordinate frame to the camera coordinate frame;
$x_r$, $y_r$, and $z_r$ are coordinates in the manipulator coordinate frame; and
d is the depth value at pixel (u, v).

The orientation of the leaflet is estimated using the relative position between its two vertices. The pitch angle is calculated by equation (3), and the yaw angle is calculated by equation (4). The roll angle is assumed to be zero.

$$\theta_{pitch} = \sin^{-1}\left( \frac{Z_{tip} - Z_{base}}{\|P_{tip} - P_{base}\|_2} \right) \qquad (3)$$

$$\theta_{yaw} = a\tan2\left( \frac{Y_{tip} - Y_{base}}{X_{tip} - X_{base}} \right) \qquad (4)$$

where $P_{tip}$ and $P_{base}$ are the coordinates of the leaflet tip and base in the world coordinate frame; and
X, Y, and Z are the x, y, and z components of the corresponding coordinates.

With the pose of several leaves estimated, one leaf is chosen from a plurality of leaves as the chosen candidate, as provided by the submodule 314 in algorithm 300. The estimated pose is validated by checking if its values are within predetermined ranges, as indicated by the query 316. If the chosen candidate meets the predetermined ranges for yaw, pitch, and roll angles, then the chosen candidate is deemed as a leaf to be used for subsequent hyperspectral imaging, multi spectral imaging, or both. If the chosen candidate does not meet the predetermined ranges for yaw, pitch, and roll angles, the algorithm first determines if there are other candidate leaves as provided in query 318. If there are other candidate leaves, the algorithm removes the prior leaf from a list of candidate leaflets, as provided by submodule 320 and return to the next such candidate leaf in submodule 314 to repeat the process of determining a valid pose. However, if there are no other candidate leaves, the algorithm returns to the image capture submodule 302 and repeats the process described above. Since soybean plants have vibrations due to airflow and self-movement, each execution of the loop described above returns different results. Each pose was estimated, validated, converted for operation in a ROS integrated Python script. The average execution time for the terminal leaf detection was 2.59s.

Figure 6B:
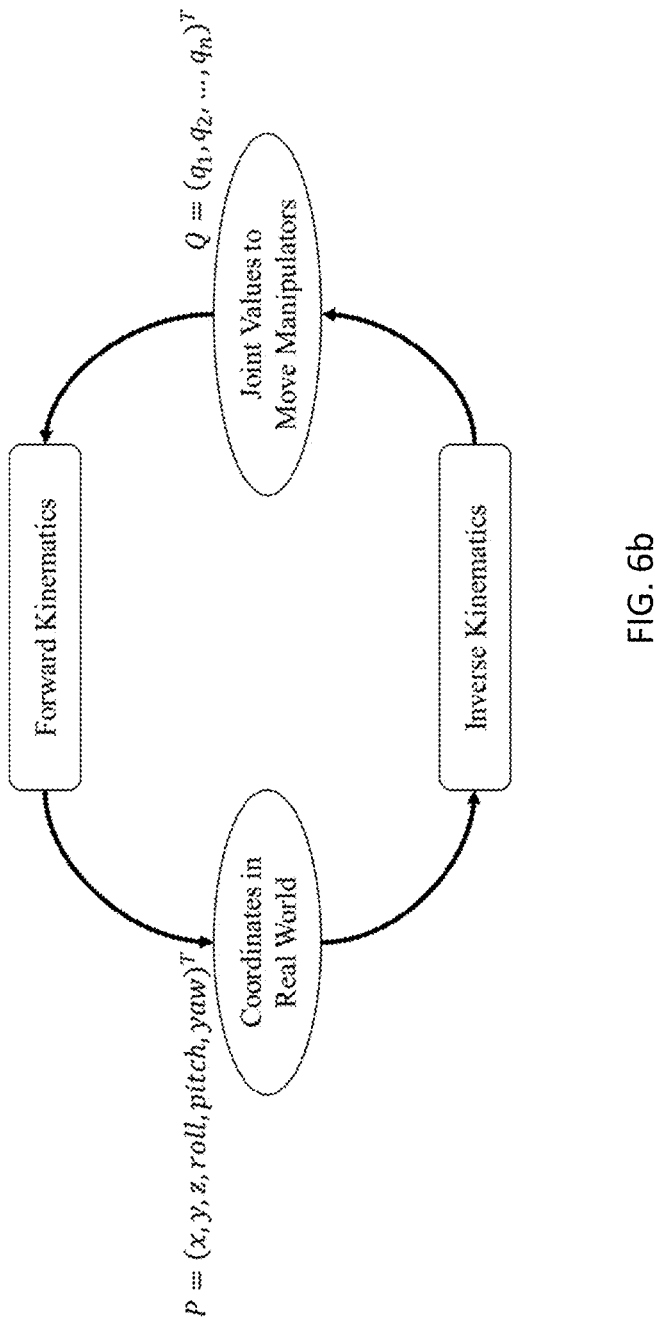
FIG. 6*b* is an operational schematic for operation of the robotic arm of FIG. 6*a* by employing inverse kinematics (IK).

Referring to FIG. 6*b*, an operational schematic is shown for operation of the robotic arm of FIG. 6*a* by employing inverse kinematics (IK). In robotics, IK is a mathematical process of computing joint values needed to place the end effector (the device at the end of a robotic arm) at a given location. For a general articulated robot with 6 degrees of freedom (DOF), as shown in FIG. 6*a*, placing the end effector to a given location is a complex challenge due to the complexity of the robot manipulator configuration. Thus, a mathematical process shown in FIG. 6*b* is needed to calculate how much each joint needs to rotate to place the end effector to a given pose (location and orientation).

However, one challenge is that there are multiple solutions for a given pose (e.g., the end effector of the robot arm shown in FIG. 6*a* can reach the exact same position by manipulating the robot arm in myriad ways). Moreover, it becomes more challenging when the manipulator needs to move among different poses. For example, if one manipulator has four solutions at each pose, there would be 16 combinations for moving between two poses, and there might only be one working combination. A geometry approach proposed in the prior art suggests adding pose indicators to specify IK results. In the development of the system of the present disclosure, line motions are needed to perform leaf feeding and scanning tasks. Pose indicators were calculated for each small motion segment to produce efficient and consistent IK results.

Figure 7:
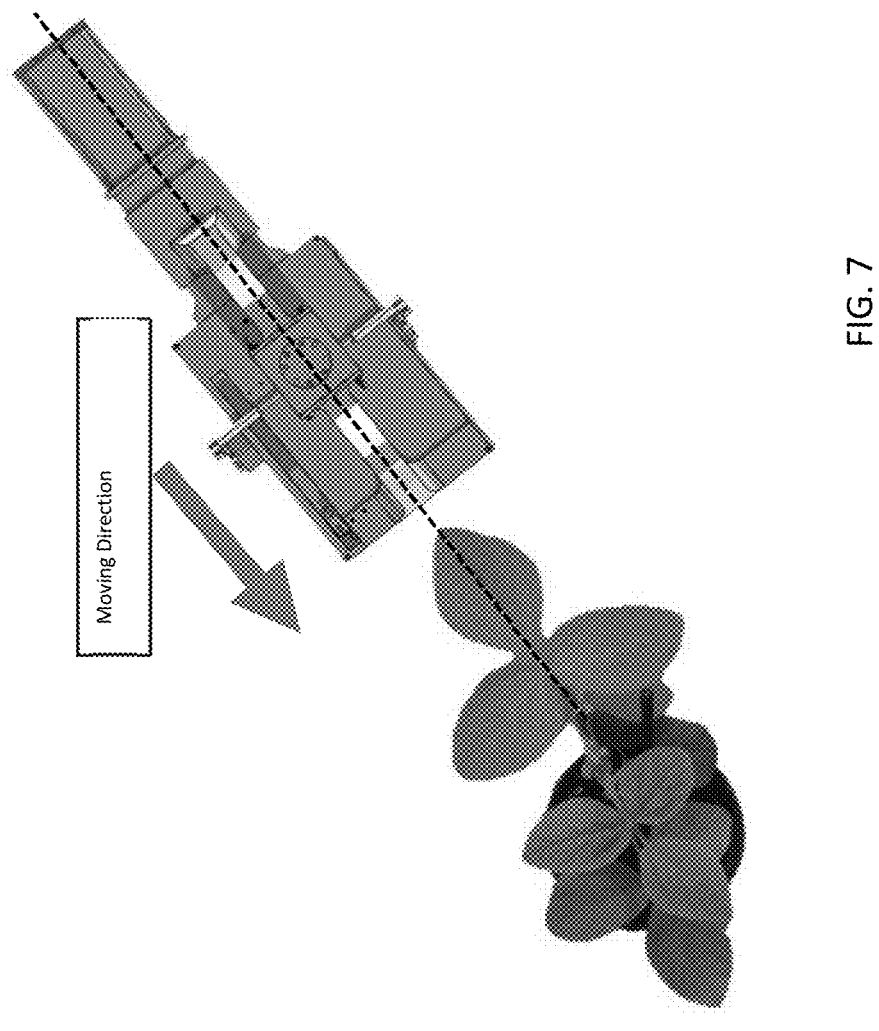
FIG. 7 is a top view schematic showing alignment of a target leaflet during leaf feeding.

Using the robotic manipulator shown in FIG. 6*a*, an operation path was generated so that the major axis of the target leaflet was aligned with a major axis of the imaging system 100 (see, e.g., FIG. 1*a*) during leaf feeding (see FIG. 7, which is a schematic showing alignment of a target leaflet during leaf feeding in top view). The planned path encountered singularities if the path passed through or was close to the z-axis of the manipulator frame. Due to the alignment requirement, the singularities may not be avoided. Alternatively, the decision equations of the configuration indicator in the geometric approach were modified to handle singularities in continuous waypoints. The configuration indicators were calculated and fixed at the beginning of each path to force the inverse kinematics to have consistent solutions.

Figure 8:
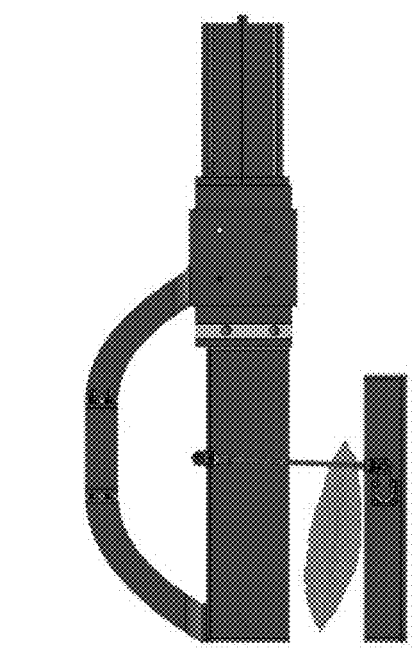
FIGS. 8 and 9 are schematics showing motion path for feeding a target leaflet into the imaging system of the present disclosure.
Figure 8:
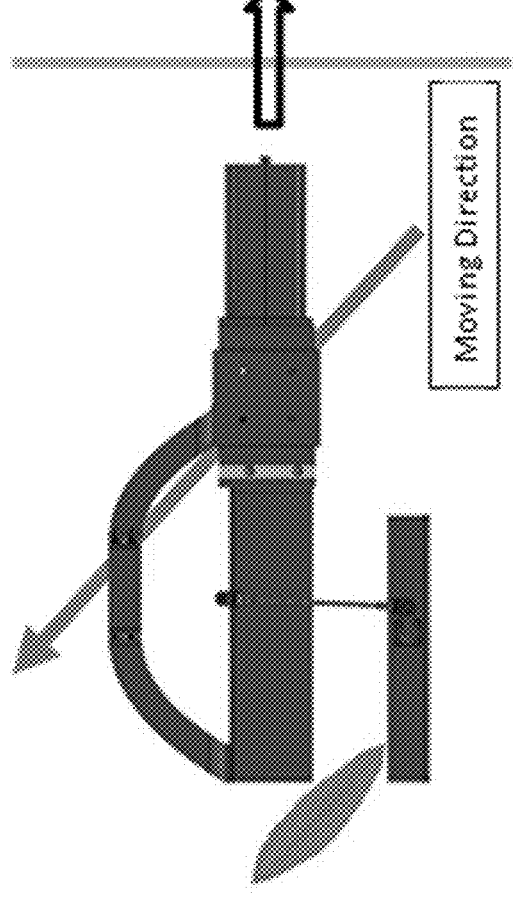
Figure 9:
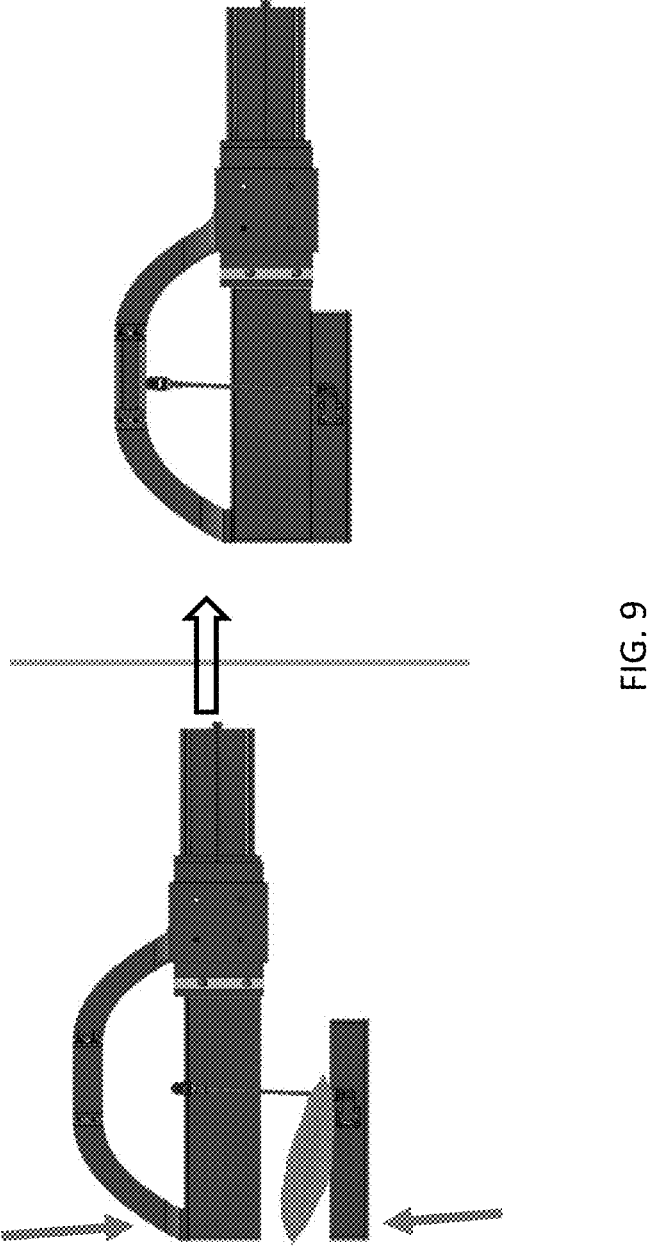

For target leaflets with a large pitch angle (inclined angle) that could not directly fit into the imaging chamber, the disclosed algorithm fed the tip of the leaflet first and slid the remainder part into the imaging system 100 (see, e.g., 1b), as provided in FIGS. 8 and 9 which are schematics showing motion path for feeding a target leaflet into the imaging system 100. Since the pitch angle of the end effector was fixed to prevent collisions, the generated path drove only the end effector's position to follow the target leaflet's pitch angle. During the leaf feeding motion, the device approached the leaflet tip first and then moved along the pitch angle of the leaflet while maintaining the device horizontally disposed. The leaflet was slid into the imaging chamber, opened and closed by a servo motor (not shown).

A controller enforced the time of the manipulator operation (see Table 1). The scanning time was also fixed due to the design of imaging system 100. The manipulator's end effector traveled the same path but in different directions in the approaching and the rehome tasks, and the feeding and the releasing tasks.

TABLE 1

Time consumption of the manipulator operation

| Task | Time (s) | Description |
| --- | --- | --- |
| Approaching | 15 | Approach a target leaflet |
| Feeding | 10 | Feed the leaflet into LeafSpec |
| Scanning | 14 | Collect a hyperspectral image of the leaflet |
| Releasing | 5 | Release and leave the leaflet |
| Rehome | 10 | Return to the home position |
| Total Operation Time with the Safety Buffer | 54 | / |
| Total Operation Time without the Safety Buffer | 44 | / |

The control and path planning algorithm was implemented on ROS MELODIC with a customized interface between the controller and the joint motors. A ROS service server was written with the modified Geometric Approach as the controller. The joint feedback values were obtained through ROS topics provided by the manufacturer. The path and corresponding waypoints were calculated in a ROS integrated Python script and were executed through ROS service messages.

Figure 10:
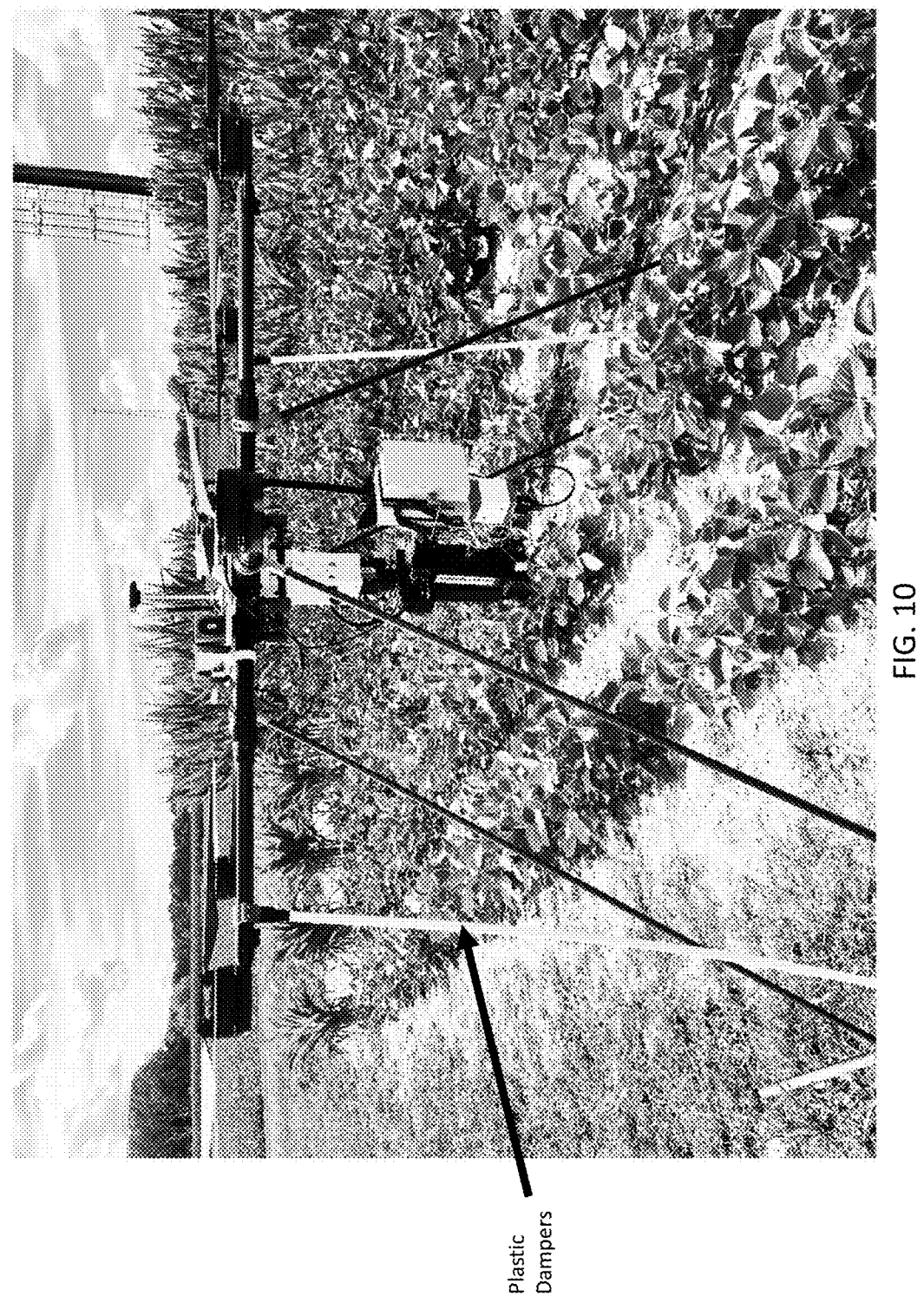
FIG. 10 is an image showing an aerial vehicle platform for transporting the robotic system of the present disclosure.

Referring to FIG. 10, an aerial vehicle for transporting the entire robotic system 200 is shown. The aerial system may be a quad-rotor aerial vehicle carrying the robotic system 200 as its payload. The aerial system would first land on top of a plant and shut down the propellers to create a wind-free environment for the sampling tasks. A single drone power source can power the entire aerial system since at no point both the robotic system 200 and the aerial vehicle are operating at the same time.

Figure 11:
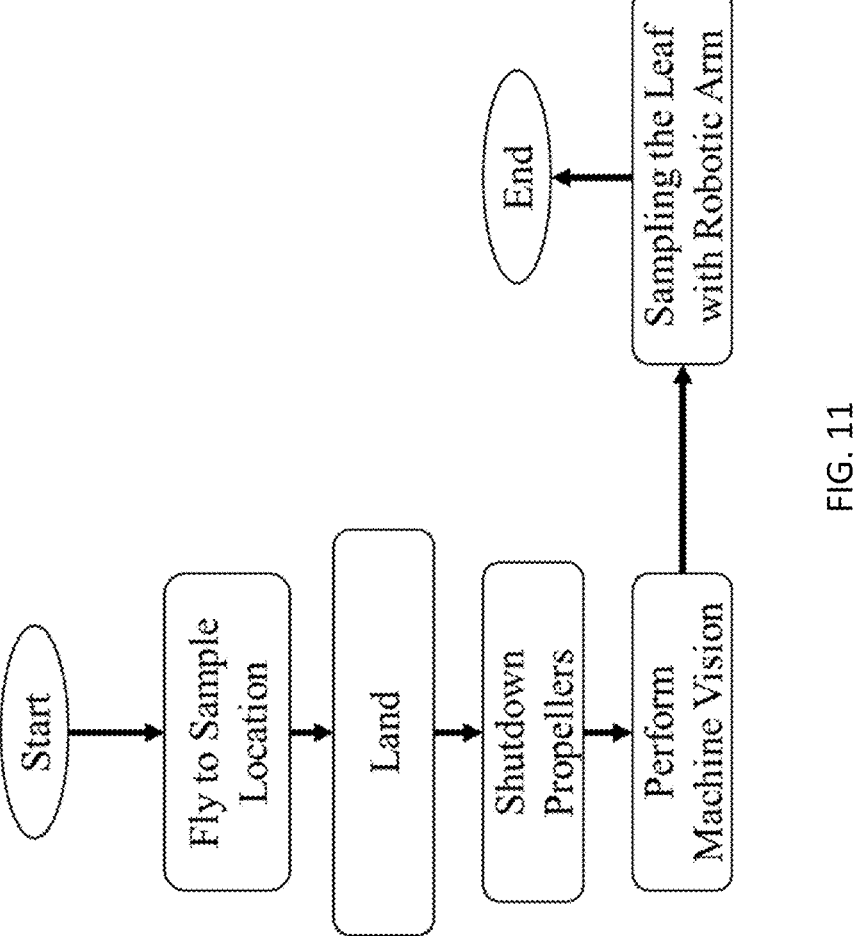
FIG. 11 is a flowchart that is used by a controller that can control the operations of the aerial platform shown in FIG. 10.

Referring to FIG. 11, a flowchart is provided that is used by a controller that can control the operations of the aerial system.

To land on top of plants to collect data, landing gear with high clearance is needed. However, extending existing landing gears according to the prior art would create fatal flight vibrations. In addition, adding solid connections between the landing gear would block the robotic arm; adding to the sides would create imbalanced force distribution. Thus, plastic dampers (identified in FIG. 10) were selected to solve the vibration problem while maintaining balanced force distribution and providing high clearance under the drone for the robotic arm operation.

It should be noted that the aerial system's center line does not align with the center line of planted rows after landing. Instead, there is an offset between the aerial system's center line and plants' center line since leaves at the plants' center line tend to have a high inclined angle. Thus, as part of the landing procedure, the plants' centerline is first detected and then the aerial system land with said offset.

While not shown, a ground-based system with autonomous mobility via a propulsion system, e.g., a vehicle with a platform coupled to a plurality of legs each terminating to a wheel configured to traverse a field, where the vehicle includes a large opening between the platform and the ground to allow the robotic system to operate as discussed above. A similar flowchart as that shown in FIG. 11 can be implemented, instead of fly to sample location, the flowchart would provide drive to sample location, and instead of shutdown propellers, the flowchart would provide either shutdown or bring to idle the propulsion system of the ground-based system.

Figure 12:
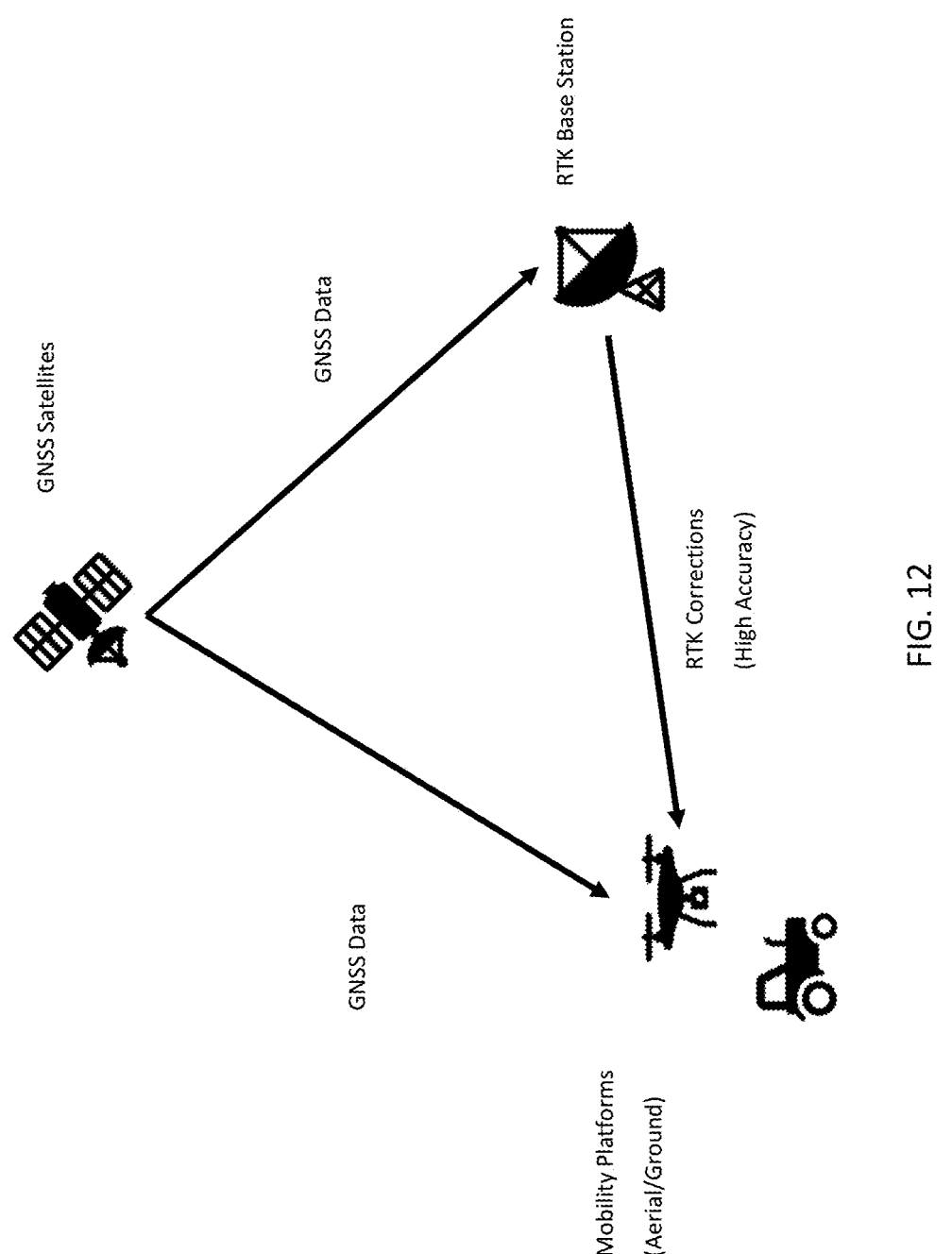
FIG. 12 is a schematic of real-time kinematics (RTK) used in an application of surveying to correct for common errors in Global Positioning System (GPS).

Referring to FIG. 12, a schematic of real-time kinematics (RTK) is provided which is the application of surveying to correct for common errors in Global Positioning System (GPS). A GPS-based system typically includes a receiver unit and uses the Global Navigation Satellites System (GNSS) to locate a position worldwide in real-time, with an accuracy of 2m. RTK has two units, a base station and a receiver. A base station is fixed at a position whose precise location is measured through other independent methods; thus, absolute position of the base station is known with a high degree of accuracy. The base station receives GNSS data and compares the received readings with its location to calculate an error associated with the GNSS in real-time. It sends the compared results, also known as corrections, to the receiver, usually by a radio frequency signal. In operation, a mobility platform, according to the present disclosure equipped with RTK receivers receive both GNSS readings from the GNSS and corrections from the base station. The corrections compensate for the error in GNSS readings to achieve centimeter-level positioning accuracy as shown in FIG. 12.

It should be noted that software provided in memory and operated by a processor/controller is within the skillset of a person having ordinary skill in the art based on the disclosed block diagrams and flowcharts.

Those having ordinary skill in the art will recognize that numerous modifications can be made to the specific implementations described above. The implementations should not be limited to the particular limitations described. Other implementations may be possible.

The invention claimed is:

1. An autonomous system for providing consistent images of leaves of plants, comprising:
a mobility system configured to move from an originating position to a position above a plant in a field;
a machine vision system having a single three dimensional (3D) depth camera, the machine vision system configured to:
a) capture an image of the plant including a leaf;
b) remove a background from the captured image;
c) identify and separate the leaf in the background-removed image;
d) identify and positionally locate a tip of the leaf from the leaf-separated image;
e) identify and positionally locate a base of the leaf;
f) estimate a pose of the leaf, wherein the pose estimation includes i) transform individual pixel coordinates of the identified and separated leaf to world coordinates, ii) determine the pitch angle of the identified leaf, and iii) determine the yaw angle of the identified leaf, wherein (ii) and (iii) are determined based on the transformed world coordinates of the individual pixels associated with the positionally located tip and positionally located base of the leaf;
a robotic system coupled to the mobility system, the robotic system comprising:
a manipulator providing a plurality of degrees of freedom, and
an imaging system having an imaging chamber defined by a housing, wherein the housing is divided into an upper case and a lower case, wherein the lower case is articulable with respect to the upper case by an imaging chamber articulation mechanism from i) an open state to ii) a closed state, wherein the articulable space between the upper case and the lower case forms an imaging chamber wherein the imaging chamber is configured to be dark when the imaging chamber articulation mechanism is in the closed state,
and one or more cameras disposed about the imaging chamber,
wherein the imaging system is coupled to the manipulator,
wherein the machine vision system is configured to control the manipulator to move the imaging system in line with the leaf according to the estimated pose and thereby articulate the lower case from the open position to the closed position when the leaf is positioned inside the imaging chamber to thereby in vivo image the leaf without causing injury to the leaf.

2. The autonomous system of claim 1, wherein the mobility system is an aerial system.

3. The autonomous system of claim 2, wherein the aerial system includes a plurality of propellers.

4. The autonomous system of claim 3, wherein the number of propellers is 3.

5. The autonomous system of claim 3, wherein the number of propellers is 4.

6. The autonomous system of claim 1, wherein the mobility system is a ground-based system.

7. The autonomous system of claim 1, wherein the manipulator provides 6 degrees of freedom.

8. The autonomous system of claim 1, further comprising a light box disposed in the lower case housing having one or more light sources.

9. The autonomous system of claim 8, the one or more cameras including a hyperspectral camera disposed within the upper case, wherein the hyperspectral camera is articulable along a first axis within the upper case via a linear actuator from i) an initial position to ii) an end position, the imaging system configured to:
a) activate the one or more light sources,
b) actuate the linear actuator to thereby linearly move the hyperspectral camera within the upper case from the initial position to the end position,
c) obtain images from the hyperspectral camera while the linear actuator moves the hyperspectral camera,
d) re-actuate the linear actuator to thereby linearly move the hyperspectral camera within the upper case from the end position back to the initial position, and
e) re-articulate the lower case to the open state, thus allowing removal of the leaf.

10. The autonomous system of claim 9, wherein the linear actuator is a rack-and-pinion system.

11. The autonomous system of claim 10, wherein the rack-and-pinion system includes a rack having a plurality of linearly disposed teeth disposed along a rail and a pinion having a plurality of circularly disposed teeth engaged with the linearly disposed teeth of the rack, wherein the pinion rotates via a pinion motor.

12. The autonomous system of claim 10, wherein the pinion motor is one of an alternating current (AC) motor, a direct current (DC) motor, and a stepper motor.

13. The autonomous system of claim 9, wherein the linear actuator is a lead screw system wherein a motor is coupled to a screw interfacing a nut where the nut is coupled to the camera.

14. The autonomous system of claim 9, wherein the linear actuator is belt driven or chain driven, wherein the camera interfaces with a gear coupled to a motor via a belt or a chain.

15. The autonomous system of claim 9, wherein the imaging chamber articulation mechanism is a slider-crank mechanism including a servo motor coupled to the upper case, a plurality of arms coupling the servo motor to the lower case, wherein the plurality of arms transform rotational motion of the servo motor to linear motion of the lower case with respect to the upper case.

16. The autonomous system of claim 15, wherein the servo motor is one of an alternating current (AC) motor, a direct current (DC) motor, and a stepper motor.

17. The autonomous system of claim 8, the one or more cameras including a multispectral camera disposed within the upper case, the imaging system configured to:

a) activate the one or more light sources, b) obtain images from the multispectral camera, and c) re-articulate the lower case to the open state, thus allowing removal of the leaf.

18. The autonomous system of claim 1, wherein the one or more cameras includes a hyperspectral camera capable of generating hyperspectral images.

19. The autonomous system of claim 1, wherein the one or more cameras includes a multispectral camera capable of generating multispectral images.

20. The autonomous system of claim 1, wherein the one or more cameras includes a hyperspectral camera capable of generating both hyperspectral and multispectral images.

21. The autonomous system of claim 1, wherein the imaging system dynamically determines whether the estimated pose of the leaf is within a threshold as the manipulator moves the imaging system towards the leaf.

22. The autonomous system of claim 1, wherein the machine vision system captures the image of the plant with a three dimensional camera.

* * * * *